(12) United States Patent
Kujawski et al.

(10) Patent No.: US 7,727,271 B2
(45) Date of Patent: Jun. 1, 2010

(54) IMPLANTABLE PROSTHESIS HAVING REINFORCED ATTACHMENT SITES

(75) Inventors: Dennis Kujawski, Warwick, NY (US); Ronald Rakos, Neshanic Station, NJ (US); Krzysztof Sowinski, Wallington, NJ (US); Jerry Q. Dong, Oakland, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/876,102

(22) Filed: Jun. 24, 2004

(65) Prior Publication Data

US 2005/0288767 A1 Dec. 29, 2005

(51) Int. Cl.
*A61F 2/06* (2006.01)
*A61F 2/82* (2006.01)

(52) U.S. Cl. .................................... 623/1.13; 623/1.35
(58) Field of Classification Search ................ 623/1.13, 623/1.44, 1.49, 1.5, 1.51, 1.52, 1.53
See application file for complete search history.

(56) References Cited

U.S. PATENT DOCUMENTS

| | | | |
|---|---|---|---|
| 3,853,462 A | 12/1974 | Smith | |
| 3,986,828 A | 10/1976 | Hoffman, Jr. et al. | |
| 4,304,010 A | 12/1981 | Mano | |
| 4,503,569 A | 3/1985 | Dotter | |
| 4,580,568 A | 4/1986 | Gianturco | |
| 4,604,762 A * | 8/1986 | Robinson | 623/1.44 |
| 4,728,328 A * | 3/1988 | Hughes et al. | 623/23.69 |
| 4,732,152 A | 3/1988 | Wallsten et al. | |
| 4,733,665 A | 3/1988 | Palmaz | |
| 4,743,252 A * | 5/1988 | Martin et al. | 623/1.44 |
| 4,886,062 A | 12/1989 | Wiktor | |
| 5,061,276 A | 10/1991 | Tu et al. | |
| 5,123,917 A | 6/1992 | Lee | |
| 5,133,742 A | 7/1992 | Pinchuk | |
| 5,151,105 A * | 9/1992 | Kwan-Gett | 623/1.32 |
| 5,178,630 A | 1/1993 | Schmitt | |
| 5,192,310 A | 3/1993 | Herweck et al. | |
| 5,209,776 A | 5/1993 | Bass et al. | |
| 5,229,431 A | 7/1993 | Pinchuk | |
| 5,522,881 A * | 6/1996 | Lentz | 623/1.13 |
| 5,549,860 A | 8/1996 | Charlesworth et al. | |
| 5,665,114 A | 9/1997 | Weadock et al. | |
| 5,665,117 A * | 9/1997 | Rhodes | 623/1.1 |
| 5,700,285 A | 12/1997 | Myers et al. | |
| 5,735,892 A | 4/1998 | Myers et al. | |
| 5,741,332 A | 4/1998 | Schmitt | |
| 5,749,880 A | 5/1998 | Banas et al. | |
| 5,800,512 A * | 9/1998 | Lentz et al. | 623/1.1 |
| 5,851,229 A | 12/1998 | Lentz et al. | |
| 5,925,075 A | 7/1999 | Myers et al. | |

(Continued)

*Primary Examiner*—Thomas J Sweet
(74) *Attorney, Agent, or Firm*—Vidas, Arrett & Steinkraus P.A.

(57) ABSTRACT

The present invention provides an implantable graft that includes an elongate graft tube having opposing ends defining an attachment site for attaching the graft to a stent. The graft further includes a reinforcement member attached adjacent to at least one of the ends of the graft for establishing a reinforced attachment site for the graft, thereby preventing elongation of a suture hole in the material. Furthermore, the present invention provides a graft wherein at least one end of the graft is folded over itself and glued or sutured to itself and/or the stent, thereby forming a reinforcement thereto.

31 Claims, 16 Drawing Sheets

U.S. PATENT DOCUMENTS

| | | |
|---|---|---|
| 5,928,279 A | 7/1999 | Shannon |
| 5,948,018 A | 9/1999 | Dereume et al. |
| 6,001,125 A | 12/1999 | Golds et al. |
| 6,036,724 A * | 3/2000 | Lentz et al. .................. 623/1.1 |
| 6,080,198 A | 6/2000 | Lentz et al. |
| 6,090,137 A | 7/2000 | Schmitt |
| 6,165,212 A | 12/2000 | Dereume et al. |
| 6,221,099 B1 | 4/2001 | Andersen et al. |
| 6,248,116 B1 * | 6/2001 | Chevillon et al. ........... 606/139 |
| 6,299,636 B1 * | 10/2001 | Schmitt et al. ............... 623/1.2 |
| 6,352,561 B1 | 3/2002 | Leopold et al. ............. 623/123 |
| 6,368,347 B1 | 4/2002 | Maini et al. |
| 6,398,802 B1 | 6/2002 | Yee ........................... 623/1.13 |
| 6,428,571 B1 * | 8/2002 | Lentz et al. .................. 623/1.4 |
| 6,440,166 B1 | 8/2002 | Kolluri |
| 6,488,705 B2 * | 12/2002 | Schmitt et al. ............. 623/1.18 |
| 6,511,506 B2 * | 1/2003 | Chevillon et al. .......... 623/1.36 |
| 6,514,283 B2 * | 2/2003 | DiMatteo et al. ........... 623/1.13 |
| 6,517,571 B1 | 2/2003 | Brauker et al. |
| 6,524,334 B1 * | 2/2003 | Thompson ................. 623/1.13 |
| 6,540,773 B2 | 4/2003 | Dong |
| 6,547,815 B2 * | 4/2003 | Myers ....................... 623/1.13 |
| 6,547,820 B1 * | 4/2003 | Staudenmeier ............. 623/1.49 |
| 6,554,855 B1 * | 4/2003 | Dong ........................ 623/1.13 |
| 6,585,758 B1 | 7/2003 | Chouinard et al. |
| 6,645,241 B1 * | 11/2003 | Strecker .................... 623/1.13 |
| 6,719,783 B2 * | 4/2004 | Lentz et al. .................. 623/1.4 |
| 6,911,042 B2 * | 6/2005 | Weadock ................... 623/1.23 |
| 6,939,372 B2 * | 9/2005 | Dong ........................ 623/1.13 |
| 7,052,513 B2 * | 5/2006 | Thompson ................. 623/1.53 |
| 7,060,684 B1 * | 6/2006 | Quijano et al. ................ 514/21 |
| 2003/0009210 A1 | 1/2003 | Sowinski et al. |
| 2003/0017775 A1 | 1/2003 | Sowinski et al. |
| 2003/0082323 A1 | 5/2003 | Venditti et al. |
| 2003/0082324 A1 | 5/2003 | Sogard et al. |
| 2003/0116260 A1 * | 6/2003 | Chobotov et al. ........... 156/217 |
| 2003/0139806 A1 * | 7/2003 | Haverkost et al. .......... 623/1.33 |
| 2003/0204241 A1 * | 10/2003 | Dong ........................ 623/1.13 |
| 2004/0033364 A1 * | 2/2004 | Spiridigliozzi et al. ... 428/411.1 |
| 2004/0167606 A1 * | 8/2004 | Chouinard ................. 623/1.13 |

* cited by examiner

IMPLANTABLE PROSTHESIS HAVING REINFORCED ATTACHMENT SITES

FIELD OF INVENTION

The present invention relates generally to a implantable prosthesis material and structure. More particularly, the present invention relates to a composite multilayer implantable graft having a tubular structure with ends of the graft defining an attachment site for attaching the graft to a stent and a reinforced member for establishing a reinforced attachment site for the prosthesis.

BACKGROUND OF RELATED TECHNOLOGY

Implantable prostheses are commonly used in medical applications. One of the more common prosthetic structures is a tubular prosthesis which may be used as a vascular graft to replace or repair or otherwise correct a damaged or diseased blood vessel. To maximize the effectiveness of such a prosthesis, it should be designed with characteristics which closely resemble that of the natural body lumen which it is repairing or replacing.

One form of a conventional tubular prosthesis specifically used for vascular grafts includes a textile tubular structure formed by weaving, knitting, braiding or any non-woven textile technique processing synthetic fibers into a tubular configuration. Tubular textile structures have the advantage of being naturally porous, which allows desired tissue ingrowth and assimilation into the body. This porosity, which allows for ingrowth of surrounding tissue, must be balanced with fluid tightness to minimize leakage during the initial implantation stage.

Grafts are typically flexible to provide compliance within a bodily lumen or within the bodily system. Such flexibility may result from the stretching of the textile yarns forming the graft. Such stretching, however, may effect the securement of the graft to the bodily lumen, which is typically secured by the use of sutures. In other words, the graft flexibility may create undesirable stresses at the suture locations of the implanted graft.

It is also well known to form a prosthesis, especially a tubular graft, from polymers such as polytetrafluoroethylene (PTFE). A tubular graft may be formed by stretching and expanding PTFE into a structure referred to as expanded polytetrafluoroethylene (ePTFE). Tubes formed of ePTFE exhibit certain beneficial properties as compared with textile prostheses. The expanded PTFE tube has a unique structure defined by nodes interconnected by fibrils. The node and fibril structure defines micropores, which facilitate a desired degree of tissue ingrowth while remaining substantially fluid-tight. Tubes of ePTFE may be formed to be exceptionally thin and yet exhibit the requisite strength necessary to serve in the repair or replacement of a body lumen. The thinness of the ePTFE tube facilitates ease of implantation and deployment with minimal adverse impact on the body.

While exhibiting certain superior attributes, ePTFE tubes are not without certain disadvantages. Grafts formed of ePTFE tend to be relatively non-compliant as compared with textile grafts and natural vessels. Further, while exhibiting a high degree of tensile strength, ePTFE grafts are susceptible to tearing. Moreover, suture hole bleeding is a problem associated with conventional ePTFE grafts. Thus, the ePTFE grafts lack many of the advantageous properties of certain textile grafts.

It is also known to use vascular grafts in conjunction with support structures. Such support structures typically come in the form of stents, which are formed of metal or polymeric materials generally formed in a tubular structure and are used to hold a vein or artery open. Stents are well known in the art and may be self-expanding or radially expandable by balloon expansion. Examples of stent/graft configurations known in the art can be seen in U.S. Pat. Nos. 5,700,285; 5,749,880; and 5,123,917, each of which are herein incorporated by reference. It is advantageous to use stent/graft configurations because the stent provides and ensures the patency of the prosthesis, while the vascular graft provides biocompatible properties in a vessel more suitable for blood to flow.

While using a vascular graft in conjunction with support structures offers certain benefits, it is also known that support structures such as a stent can result in axial elongation and radial shrinkage of the graft material due to the stresses applied to the graft material by the support structure during the contraction and expansion of the support structure. Such stent/graft designs consist of a stent and covering. In certain situations, the covering may be attached by stitching or suturing the covering to the stent wires. In such embodiments, one of the primary failure modes of stent grafts is the loss of covering integrity at suture attachment sites. At this attachment site the textile or other material is stressed either during loading or over time by the pulsate blood flow and changing aneurysm morphology. The stresses over time cause the suture or stitching material to elongate the suture hole in the covering. Depending on the strength of the base material the holes may elongate to a point whereby the device may lose integrity.

It is apparent that conventional textile prostheses as well as ePTFE prostheses have acknowledged advantages and disadvantages. Neither of the conventional prosthetic materials exhibits fully all of the benefits desirable for use as a vascular prosthesis.

It is therefore desirable to provide an implantable material and structure, preferably in the form of a tubular vascular prosthesis, which achieves many of the above-stated benefits without the resultant disadvantages associated therewith.

SUMMARY OF THE INVENTION

The present invention provides an implantable device having reinforced attachment sites.

In a first embodiment of the invention, an implantable prosthesis is provided. The implantable prosthesis includes an elongate tubular graft and a reinforcement member. The elongate tubular graft has opposed ends and a tubular wall therebetween having inner and outer wall surfaces, the ends defining an attachment site for attaching the graft to a stent. The reinforcement member is attached adjacent to at least one of the ends for reinforcing the attachment site thereat.

In a second embodiment of the invention, an implantable medical device is provided. The implantable medical device includes a generally tubular stent, an elongate tubular graft and a reinforcement member. The generally tubular stent has openings in its wall structure and opposed first and second stent open ends. The elongate tubular graft has opposing ends and a tubular wall therebetween having inner and outer wall surfaces, the graft covering the stent by extending longitudinally from the first stent open end to the second step open end to define a stent/graft prosthesis, and the opposing graft ends defining an attachment site for attaching the graft to the stent. The reinforcement member is attached adjacent to at least one of the ends for reinforcing the attachment site thereat for the stent/graft prosthesis.

In a third embodiment of the invention, a method of forming an implantable prosthesis is provided. The method includes the steps of: providing an elongate tubular graft having opposed ends and a tubular wall therebetween having inner and outer wall surfaces, the opposed ends defining an attachment site for attaching the graft to a stent; and bonding a reinforcement member adjacent to at least one of the opposed graft ends for reinforcing the attachment site thereat. The method further includes the step of attaching a stent to the graft at the reinforced attachment site, wherein the stent stretches longitudinally across the opposed graft ends to form a stent/graft prosthesis.

DETAILED DESCRIPTION OF THE INVENTION

Figure 1:
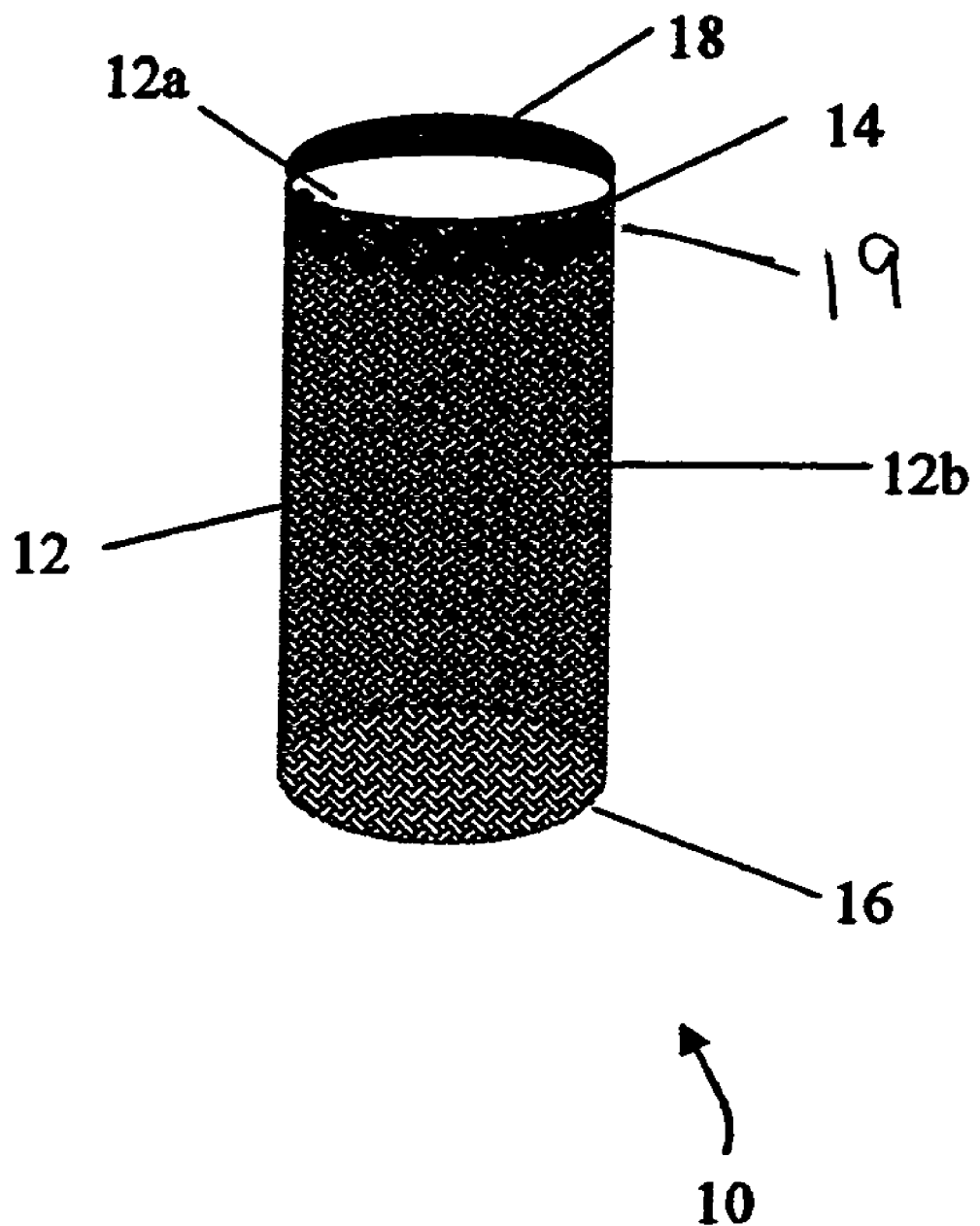
FIG. 1 is a perspective view of a tubular graft of the present invention.

One aspect of the present invention relates to an implantable medical device including an elongate tubular graft and a reinforcement member for establishing a reinforced attachment site for preferably attaching the graft to a stent. In one desired embodiment, the reinforcement member is located at each of the two opposing graft ends for reinforcing the attachment sites of graft or hybrid graft materials that are used as stent-graft coverings. The graft including the reinforcement member can be an ePTFE graft, textile graft, or a hybrid graft. For example, in one desired embodiment, the reinforced graft is a hybrid graft including an inner ePTFE layer and an outer textile layer. The hybrid graft layers can be secured together, preferably by an elastomeric bonding agent. The prosthesis of the present invention may include ePTFE-lined textile grafts, and ePTFE grafts including a textile covering.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. In this disclosure, the material and structure of the present invention may be described with respect to its application in the structure of a graft or stent-graft prosthesis device.

The composite medical device of the present invention may be a hollow tubular graft 10, as illustrated in FIG. 1. The graft 10 is a single lumen device defined by a cylindrical wall 12 with a first open end 14 and a second open end 16. The first and second open ends 14 and 16 respectively define attachment sites for attaching the graft to a stent. The wall 12 also includes inner and outer surfaces/layers 12a and 12b, respectively. In the embodiment shown, outer layer 12b of cylindrical wall 12 of prosthesis 10 is of a textile construction. Inner layer 12a can be formed of a polymer, such as ePTFE. Inner layer 12a can be a tube or a sheet, wrap, or film-like tube. The hybrid textile/polymeric prosthesis shown may have a stent associated with it to provide a stent/graft device. Reinforcement member 18 is shown attached to end 14 for reinforcing the attachment site thereat for attaching the graft to a stent. In the present figure, reinforcement member 18 is a ring of knitted or woven textile material that has been bonded to the inner layer 12a of a hybrid graft, at the graft end(s).

The tubular graft 10 defines an inner lumen extending longitudinally therethrough. The inner lumen allows the passage of a fluid, e.g., blood through the prosthesis subsequent to deployment in the body. Graft 10 can be tailored to have any desired length and internal diameter to fit the intended application. Various shapes and configurations may also be employed. For example, bifurcations, extensions off a main tubular trunk section, tapers, and stepped and flared grafts are among the many shapes and configurations useful in the present invention.

Specifically, the outer covering/layer 12b may be formed of a textile material. The textile material of the present invention may be formed from synthetic yarns that may be flat, shaped, twisted, textured, pre-shrunk or un-shrunk. Preferably, the yarns are made from thermoplastic materials including, but not limited to, polyesters, polypropylenes, polyethylenes, polyurethanes, polynaphthalenes, polytetrafluoroethylenes and the like. The yarns may be of the multifilament, monofilament or spun types. In most vascular applications, multifilaments are preferred due to the increase in flexibility. Where enhanced crush resistance is desired, the use of monofilaments have been found to be effective. As is well known, the type and denier of the yarn chosen are selected in a manner which forms a pliable soft tissue prosthesis and, more particularly, a vascular structure have desirable properties.

The inner layer 12a may be formed of expanded polytetrafluoroethylene (ePTFE). The ePTFE layer may be produced from the expansion of PTFE formed in a paste extrusion process. The PTFE extrusion may be expanded and sintered in a manner well known in the art to form ePTFE having a microporous structure defined by nodes interconnected by elongate fibrils. The distance between the nodes, referred to as the internodal distance (IND), may be varied by the parameters employed during the expansion and sintering process.

The ePTFE of the present invention may also be "ultrathin" ePTFE as described in commonly-owned applications, U.S. Ser. Nos. 10/012,825 and 10/012,919, the disclosures of which are herein incorporated by reference.

The graft 10 may be used in various vascular applications in planar form or in tubular form as a graft. The textile surface 12b may be designed as a tissue contacting surface in order to promote enhanced cellular ingrowth, which contributes to the long term patency of the graft. The ePTFE surface 12a may be used as a blood contacting surface so as to minimize leakage and to provide a generally anti-thrombogetic surface. While this is the preferred usage of the composite graft of the present invention, in certain situations, the layers may be reversed where indicated.

As mentioned above, the attachment sites are defined by the first and second open ends 14 and 16 respectively, that attach the graft 10 to the stent. The attachment sites allow the graft 10 to be stitched 19 or sutured to the stent (not shown) at one or both of the open ends 14 and 16 of the graft 10. Typically, a stent graft device having attachment sites is inserted into the delivery system for treatment of the patient. During the loading of the device, or over time by the pulsate blood flow and changing aneurysm morphology, the textile or other material at the attachment site is stressed. The stresses over time cause the suture or stitching material to elongate the suture hole in the stent/graft covering. In order to prevent the hole from extending, a reinforcement at the covering is required for reinforcing the attachment sites. The graft 10 therefore includes a reinforcement member 18, which can be attached to the inner layer 12a adjacent to the first open end 14. Preferably, reinforcement member 18 is attached at both of open ends 14 and 16 of the graft 10. The reinforcement member 18 reinforces the attachment site of the graft 10 that is used as stent-graft covering to prevent the elongation of the hole in the covering. The reinforcement member 18 is preferably made of textile material which may be knitted, braided or woven. In one embodiment, the reinforcement member 18 is bonded to an inner ePTFE layer of a graft, as will be described in greater detail below.

Figure 2:
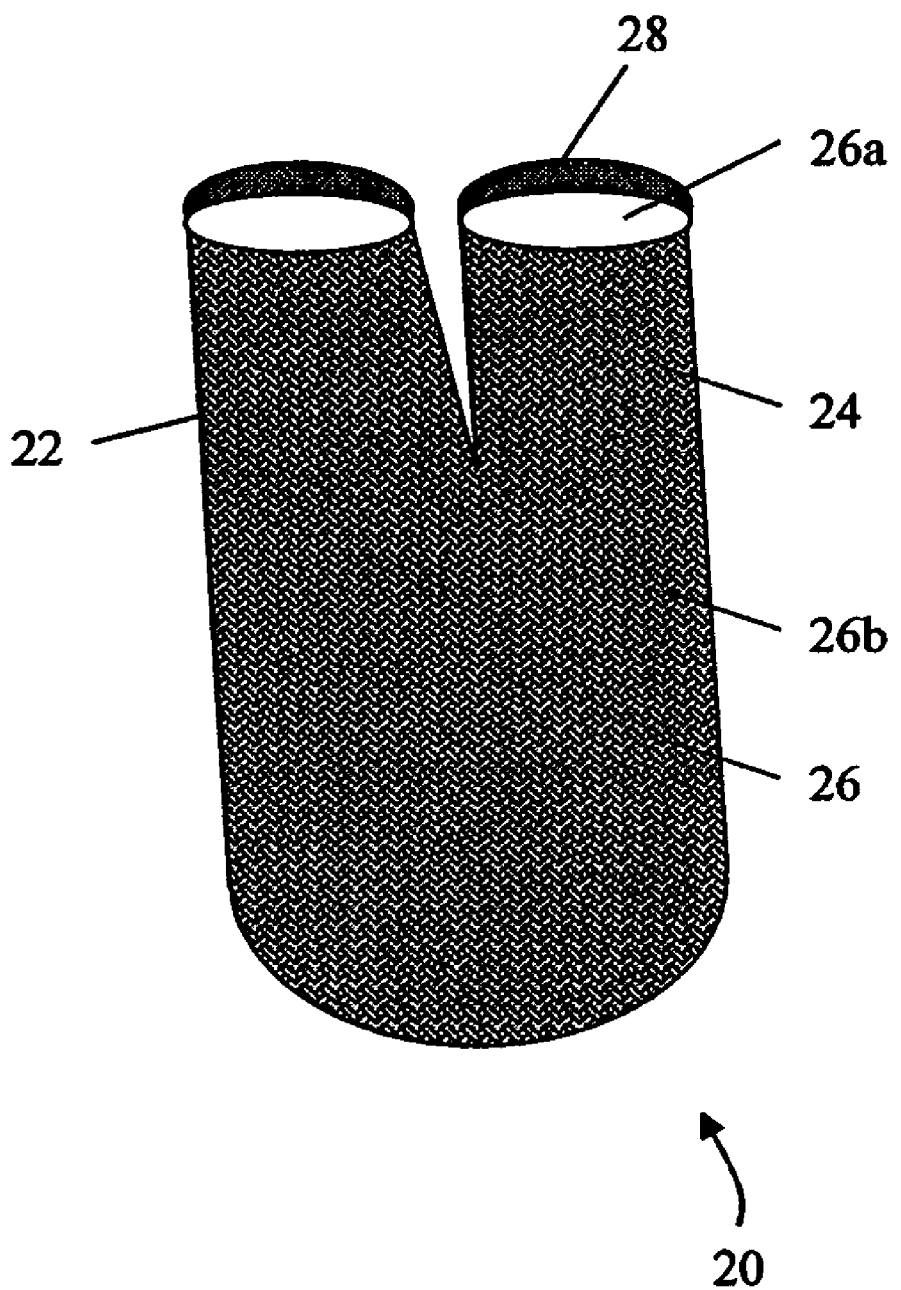
FIG. 2 is a perspective view of a bifurcated tubular graft of the present invention.

As mentioned above, the present invention is not limited to a single lumen graft. For example, a multi-lumen graft, such as bifurcated prosthesis 20, may suitably be provided with a composite textile construction. As depicted in FIG. 2, bifurcated graft 20 includes two hollow tubular legs 22, 24 and a main hollow tubular body 26. Tubular legs 22, 24 and hollow tubular body 26 include inner and outer surfaces/layers 26a and 26b, respectively. In one desired embodiment, outer surface layer 26b is of a textile material, and inner surface layer is of ePTFE. It is noted that the present invention is not limited to tubular graft, and non-tubular medical devices are also encompassed by the present invention.

Referring again to FIG. 1, in one desired embodiment, textile layer 12b is secured to the surface of ePTFE layer 12a which has been coated with a bonding agent (not shown). The textile layer 12b is secured by placing it in contact with the bonding agent. The bonding agent is preferably applied in solution by a spray coating process. However, other processes may be employed to apply the bonding agent. The bonding agent is shown in a cross-section view of the graft in FIGS. 3a and 3b described hereinbelow.

Figure 3A:
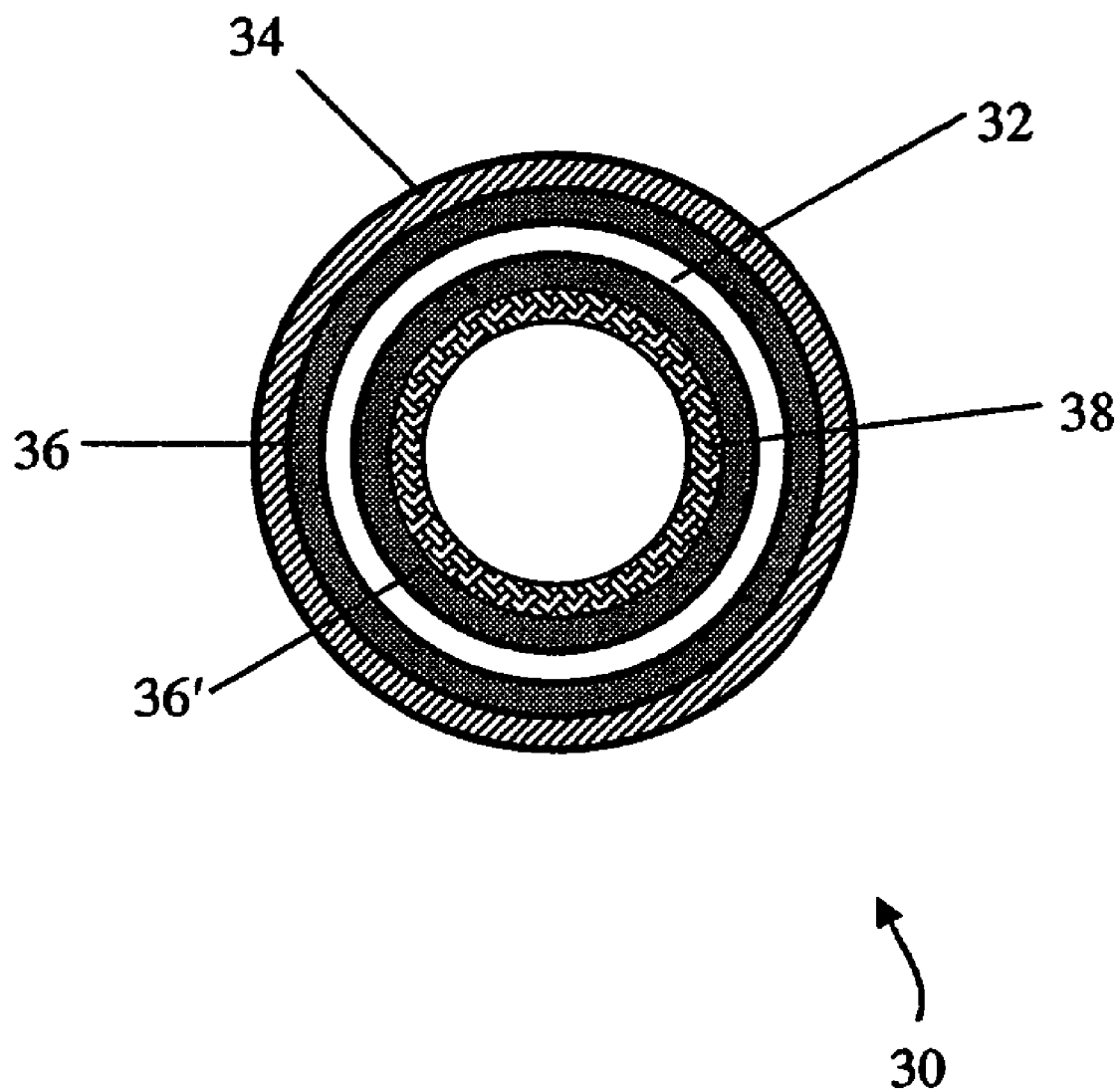
FIG. 3a shows a schematic cross-section of one of the embodiments of the tubular graft of the present invention.

With reference to FIG. 3a, there is shown one embodiment of a cross-section view of the multi-layered graft of the present invention taken through one of the attachment sites. A graft 30 is shown having an inner ePTFE layer 32 being bonded to an outer textile layer 34 (e.g., knit, woven or braid) with a layer of bonding agent 36. Also, a reinforcement member 38 is provided, which in this embodiment is attached to the ePTFE layer 32 by an inner layer of bonding agent 36'. The reinforcement member 38 is preferably a ring of knitted or woven textile material.

Figure 3B:
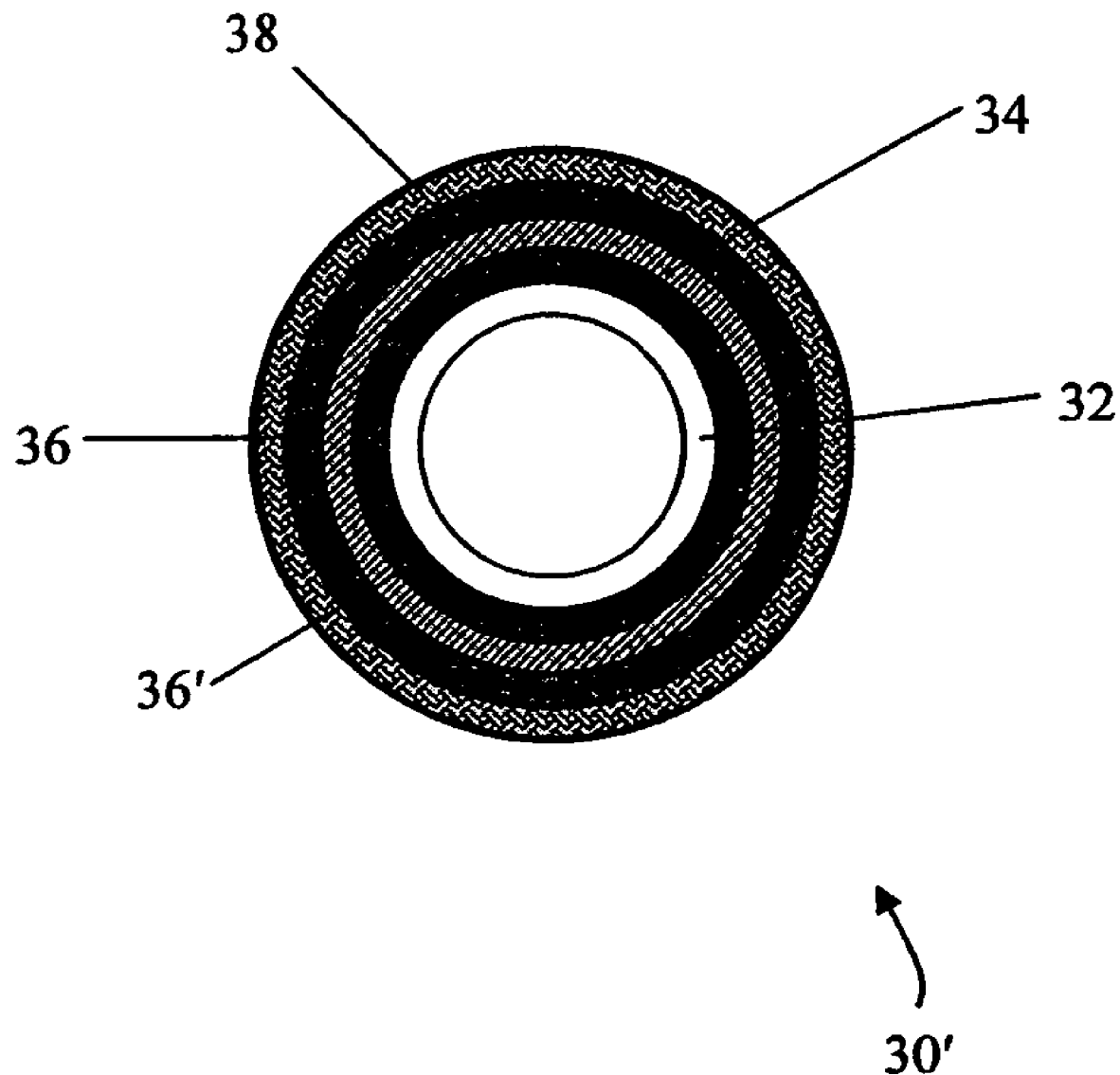
FIG. 3b shows a schematic cross-section of an alternate embodiment of the tubular graft of the present invention.

With reference to FIG. 3b, there is shown an alternate embodiment of a cross-section view of the multi-layered graft of the present invention also taken through one of the attachment sites. The graft 30, as shown in FIG. 3b, includes the reinforcement member 38, which in this embodiment is attached to the outer textile layer 34 (e.g., knit, woven or braid) by a layer of bonding agent 36. It is also possible to attach a textile reinforcement member 38 to a textile graft layer via ultrasonic bonding. The inner ePTFE layer 32 is shown bonded to the outer textile layer 34 with the inner layer of bonding agent 36'.

As described above and as shown in FIGS. 3a and 3b, the reinforcement member can be attached to the inner wall surface of the graft or the outer wall surface of the graft. However, it is noted that it is also well within the contemplation of the present invention that reinforcement members can be attached to both the inner and outer wall surfaces of the graft (not shown) via adhesive bonding or other suitable methods disclosed herein.

In the present invention, the bonding agent may include various biocompatible, elastomeric bonding agents such as urethanes, styrene/isobutylene/styrene block copolymers (SIBS), silicones, and combinations thereof. Other similar materials are contemplated. Most desirably, the bonding agent may include polycarbonate urethanes identified by the trade name CORETHANE®. This urethane is provided as an adhesive solution with preferably 7.5% Corethane, 2.5, in dimethylacetamide (DMAc) solvent.

The term "elastomeric" as used herein refers to a substance having the characteristic that it tends to resume an original shape after any deformation thereto, such as stretching, expanding, or compression. It also refers to a substance which has a non-rigid structure or flexible characteristics in that it is not brittle, but rather has compliant characteristics contributing to its non-rigid nature.

The polycarbonate urethane polymers particularly useful in the present invention are more fully described in U.S. Pat. Nos. 5,133,742 and 5,229,431, which are incorporated in their entirety herein by reference. These polymers are particularly resistant to degradation in the body over time and exhibit exceptional resistance to cracking in vivo. These polymers are segmented polyurethanes which employ a combination of hard and soft segments to achieve their durability, biostability, flexibility and elastomeric properties.

The bonding agents of the present invention, particularly the materials noted above and, more particularly, polycarbonate urethanes, such as those formed from the reaction of aliphatic macroglycols and aromatic or aliphatic diisocyanates, are elastomeric materials which exhibit elastic properties. Conventional ePTFE is generally regarded as an inelastic material, i.e., even though it can be further stretched, it has little memory. Therefore, conventional ePTFE exhibits a relatively low degree of longitudinal compliance. Also, suture holes placed in conventional ePTFE structures do not self-seal, due to the inelasticity of the ePTFE material. By applying an elastomeric coating to the ePTFE structure, both longitudinal compliance and suture hole sealing are enhanced.

The composite ePTFE-lined textile graft is desirably formed as follows. A thin ePTFE tube is formed in a conventional forming process, such as by tubular extrusion or by sheet extrusion, where the sheet is formed into a tubular configuration. The ePTFE tubular structure may be longitudinally compressed in the axial direction to between 1% to 85% of its length to relax the fibrils of the ePTFE. The amount of desired compression may depend upon the amount of longitudinal expansion that was imparted to the base PTFE green tube to create the ePTFE tube. Longitudinal expansion and compression may be balanced to achieve the desired properties. This is done to enhance the longitudinal stretch properties of the resultant graft. The longitudinal compression process can be performed either by manual compression or by thermal compression. Following the longitudinal compression process, the ePTFE tube is placed over a stainless steel mandrel and the ends of the tube are secured. The ePTFE tube is then spray coated with an adhesive solution of anywhere from 1%-15% Corethane® urethane, 2.5 in DMAc. As noted above, other adhesive solutions may also be employed. The coated ePTFE tube is placed in an oven heated in a range from 18° C. to 150° C. for 5 minutes to overnight to drive off the solution. If desired, the spray coating and drying process can be repeated multiple times to add more adhesive to the ePTFE tube.

The compressed ePTFE tube is then covered with a thin layer of the textile tube. One or more layers of elastic tubing, preferably silicone, is placed over the composite. This holds the composite together and assures that there is complete contact and adequate pressure. The assembly is then placed in a 205° C. oven for approximately 10-20 minutes to bond the layers together to form the ePTFE lined textile graft. The bonding process is more fully described in commonly owned U.S. patent application Ser. No. 10/166,842, entitled, "Composite ePTFE/Textile Prosthesis," filed on Jun. 11, 2002, and U.S. patent application Ser. No. 10/643,315, entitled, "Pleated Composite ePTFE/Textile Hybrid Covering" filed on Aug. 19, 2003, the disclosure of which are incorporated by reference herein.

Thereafter, the ePTFE lined textile graft may optionally be crimped along the tubular surface thereof to impart longitudinal compliance, kink resistance and enhanced handling characteristics, if desired. The crimp may be provided by placing a coil of metal or plastic wire around a stainless steel mandrel. The graft is slid over the mandrel and the coil wire. Another coil is wrapped around the assembly over the graft to fit between the spaces of the inner coil. The assembly is then heat set and results in the formation of the desired crimp pattern. It is further contemplated that other conventional crimping processes may also be used to impart a crimp to the ePTFE textile graft if so desired.

In order to further enhance the crush and kink resistance of the graft, the graft may preferably be wrapped with a polypropylene monofilament if desired. This monofilament is wrapped in a helical configuration and adhered to the outer surface of the graft either by partially melting the monofilament to the graft or by use of an adhesive.

Regarding the process used to reinforce the hybrid graft described above or other graft materials, the ends of the graft can sprayed on the inside graft surface or layer with a Corethane® or other adhesive solution and allowed to dry. A reinforcement member (e.g., a textile ring) is then desirably placed inside the inner graft surface at the coated end(s), as shown in FIG. 3a, and bonded with heat and pressure using a similar method to that used when forming the hybrid graft.

Specifically, the reinforcement member 18, which is preferably comprised of a layer of textile material, and desirably in a shape of a ring, is placed adjacent to at least one of the opposing ends of the graft for reinforcing the attachment site thereat for attaching a graft to a stent. In one desired embodiment, reinforcement members are positioned adjacent to both ends of the graft. It is also within the contemplation of the present invention that reinforcement members can be located throughout the stent-graft covering. As described above, a textile ring can be bonded to the stent/graft preferably using both pressure and heat. The amount of pressure applied to bond the textile ring to the regions of covering is typically between 2.5 psi and 50 psi, but can also be lower. Alternatively, one or more layers of elastic tubing, preferably silicone, is then placed over the composite structure. This holds the composite structure together and assures that complete contact and adequate pressure is maintained for bonding purposes. Even though the process described above is with reference to a ring, it is to be noted that the reinforcement member can be in different forms. For example, a patch of textile material can be used for reinforcement at the suture location. The bonding process is more fully described in commonly owned U.S. patent application Ser. No. 10/166, 842, entitled, "Composite ePTFE/Textile Prosthesis," filed on Jun. 11, 2002, and U.S. patent application Ser. No. 10/643, 315, entitled, "Pleated Composite ePTFE/Textile Hybrid Covering" filed on Aug. 19, 2003, the disclosure of which are incorporated by reference herein.

Typically, the graft of the present invention would be attached to a support structure such as a stent which will be described in greater detail with reference to FIG. 4 below. In one desired embodiment, the stent is located on the inside surface of the tubular graft (i.e., underlying the graft covering) and the reinforcement member is attached to the graft end(s). However, the stent can also be disposed within the graft itself. Preferably, the stent is attached to the open ends 14 and 16, which define the attachment sites. At the attachment sites, the graft 10 may be sutured or stitched to the stent along one of the ends 14 and 16 respectively. The graft desirably covers the stent by extending longitudinally from open end 14 to open end 16. The stent provides additional structural stability to the implantable medical device. The stent, which is preferably formed of metal or polymeric materials, is generally formed in a tubular structure and are used to hold a vein or artery open. Stents may be self-expanding or radially expandable by balloon expansion.

The ePTFE textile graft having reinforced attachment sites, which is provided by the present invention, exhibits advantages over conventional ePTFE textile grafts in that the reinforcement member, e.g. textile ring, reinforces the attachment sites of the graft so the device maintains its integrity. A reduction in the elongation of suture hole is seen at the attachment site which further prevents tear in ePTFE.

The present invention is not limited to adding a textile reinforcement at the attachment sites of the graft prior to implantation of the graft device with a body lumen. The reinforcing suture attachment sites can be placed on already implanted open repair vascular grafts by performing an open surgery.

Figure 4A:
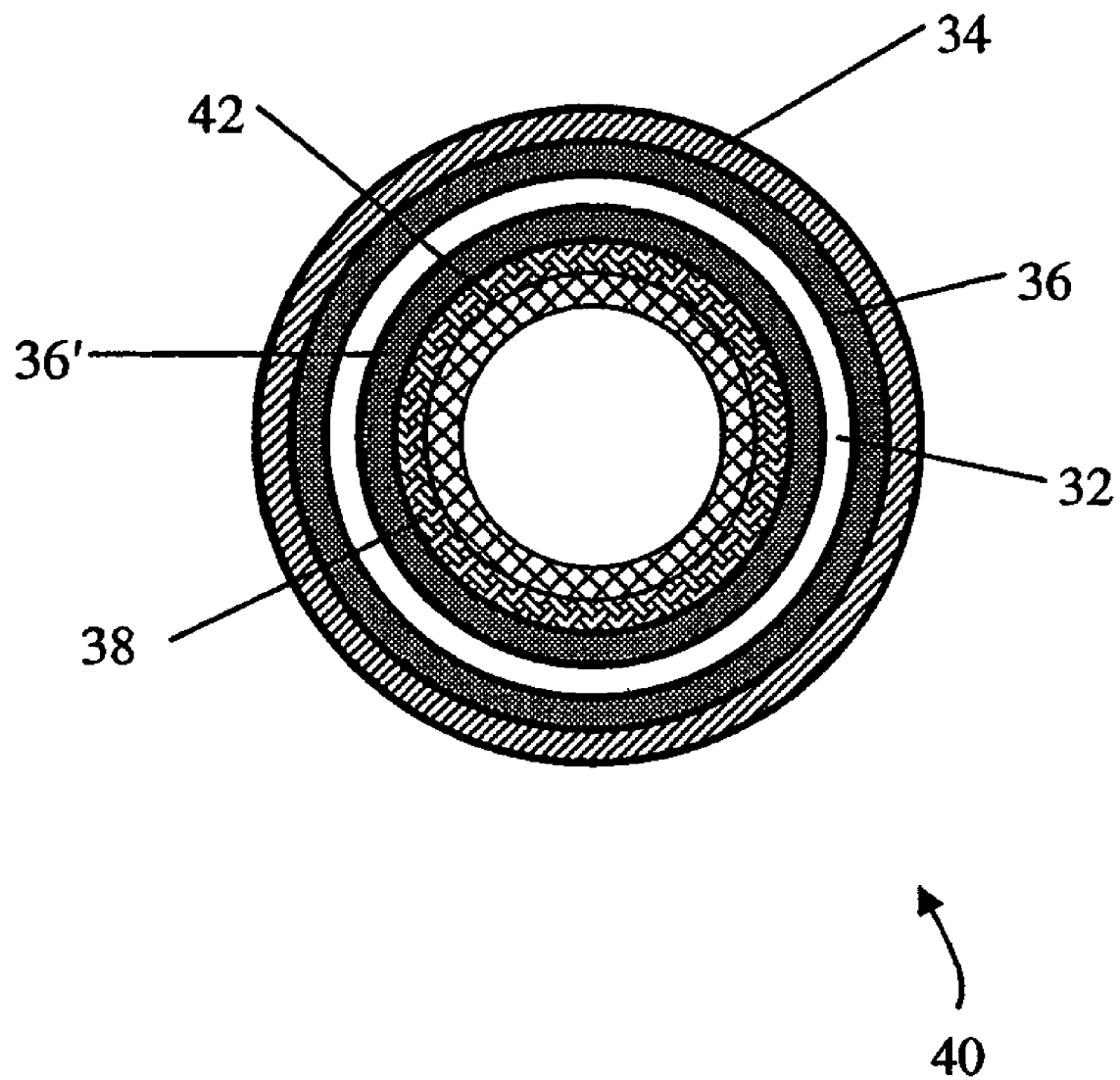
FIGS. 4a-4e show cross-section views of various embodiments of the tubular stent/graft of the present invention.
Figure 4B:
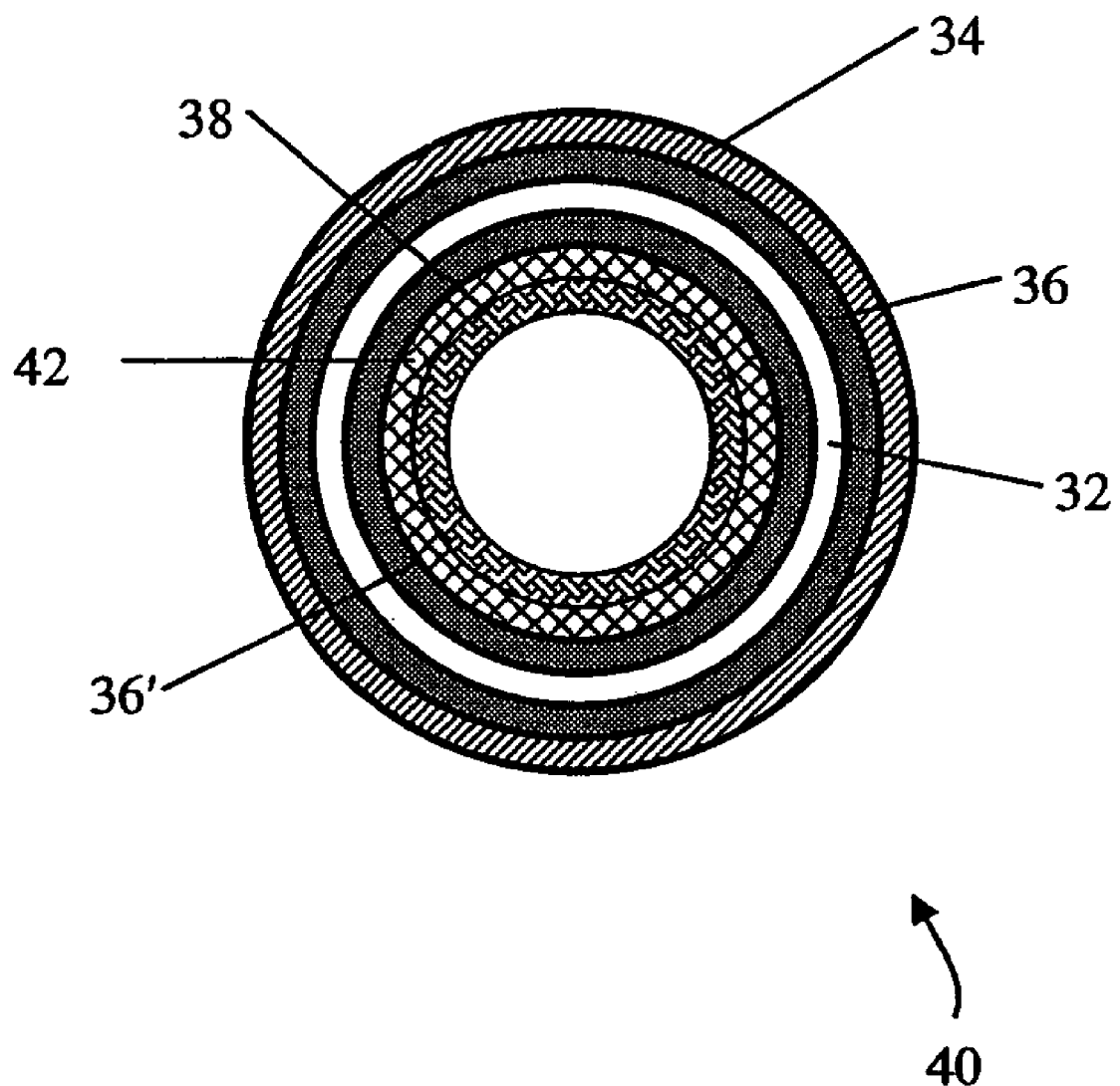
Figure 4C:
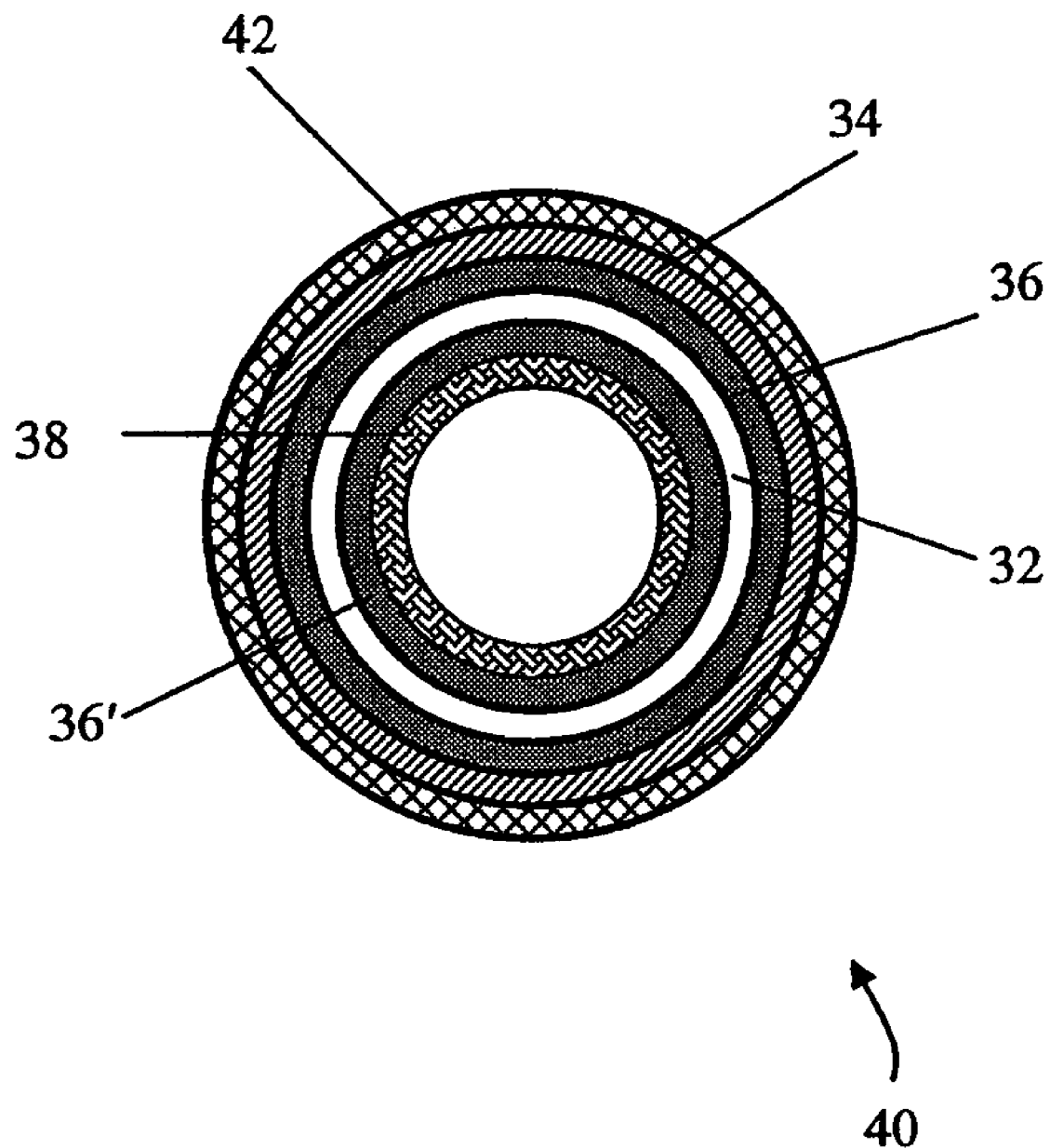

With reference to FIGS. 4a, 4b, and 4c there is shown a cross-section view of one embodiment of the stent/graft of the present invention with the reinforcement member 38 securely attached to the inner layer of the graft. The stent/graft 40 comprises all the layers as shown in FIG. 3a with an addition of a tubular support structure, preferably a stent 42 as shown in FIGS. 4a, 4b, and 4c. In FIGS. 4a and 4b, the stent 42 is located on the inside surface of the graft. As mentioned above, the stent can alternatively be disposed within the graft itself (not shown). The stent 42 is radially expandable and is capable of maintaining patency of the graft 30 in a bodily vessel. Also, included in FIG. 4a is the reinforcement member 38 preferably a textile material, securely attached to the inner wall surface of the ePTFE layer 32. Optionally, as shown in FIG. 4b, the reinforcement member 38 is securely attached to the stent 42. Stent 42 may be attached to the adjoining graft through mechanical securement or bonding. Mechanical securement includes, but is not limited to, the use of sutures, anchoring barbs, textile cuffs, and the like. Bonding includes, but is not limited to, chemical bonding, for instance adhesive bonding, thermal bonding or welding, ultrasonic bonding or welding, and the like. The use of sutures and these bonding techniques may also be suitably used to secure different textile portions to one and the other, such as textile layer 34 being secured to the reinforcement member 38 also of textile material.

Alternatively, the stent 42 can preferably be located on the outside surface of the graft as shown in cross-section view of the stent/graft 40 in FIG. 4c to allow for a smooth lumen and may given the graft enhanced support. Additionally with the stent wires 42 outside the graft also may prevent guidewire entrapment during the deployment of the stent/graft 42 on follow-up or additional procedures. Note the reinforcement member 38 is securely attached to the inner layer of the graft.

Figure 4D:
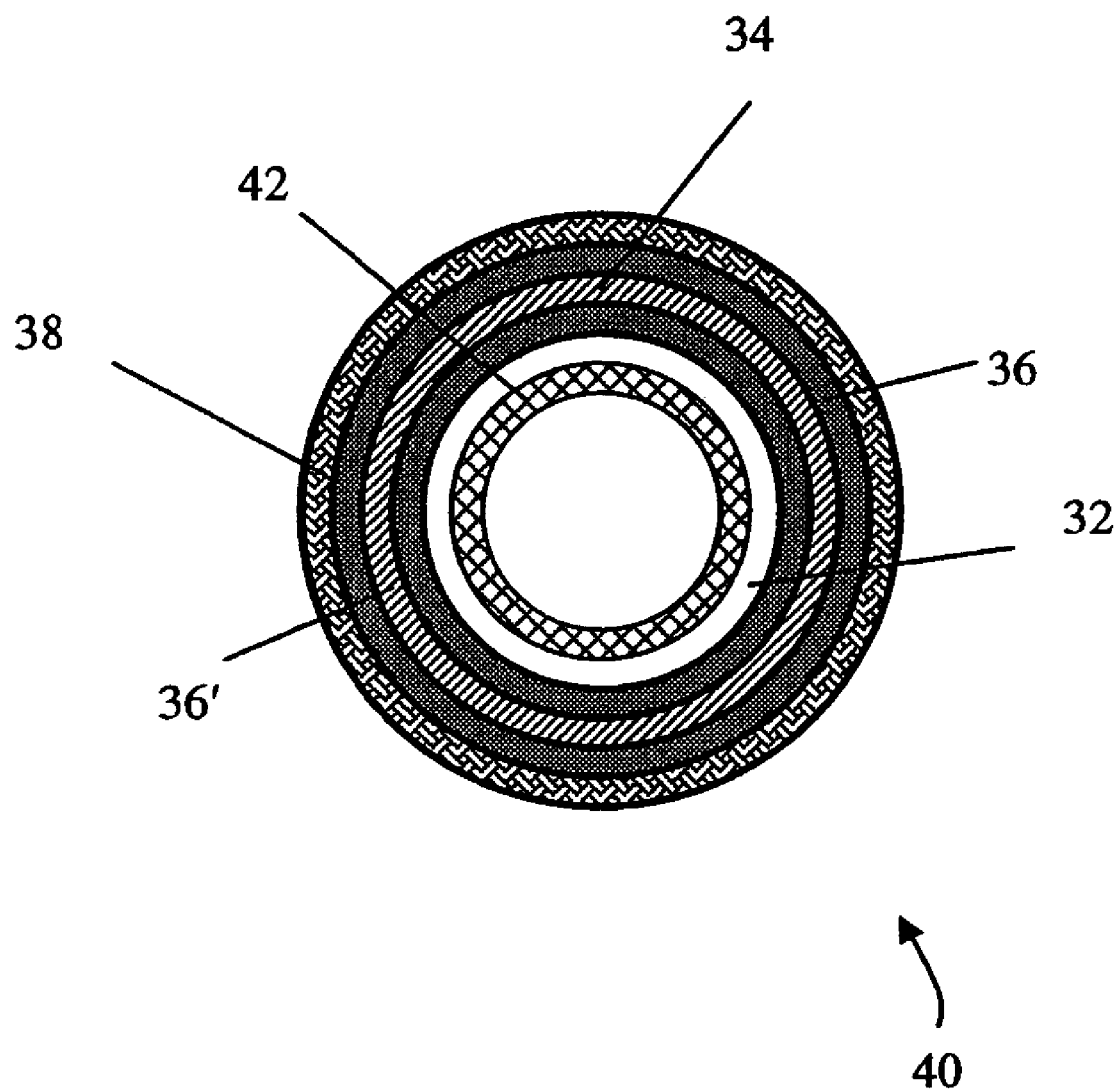
Figure 4E:
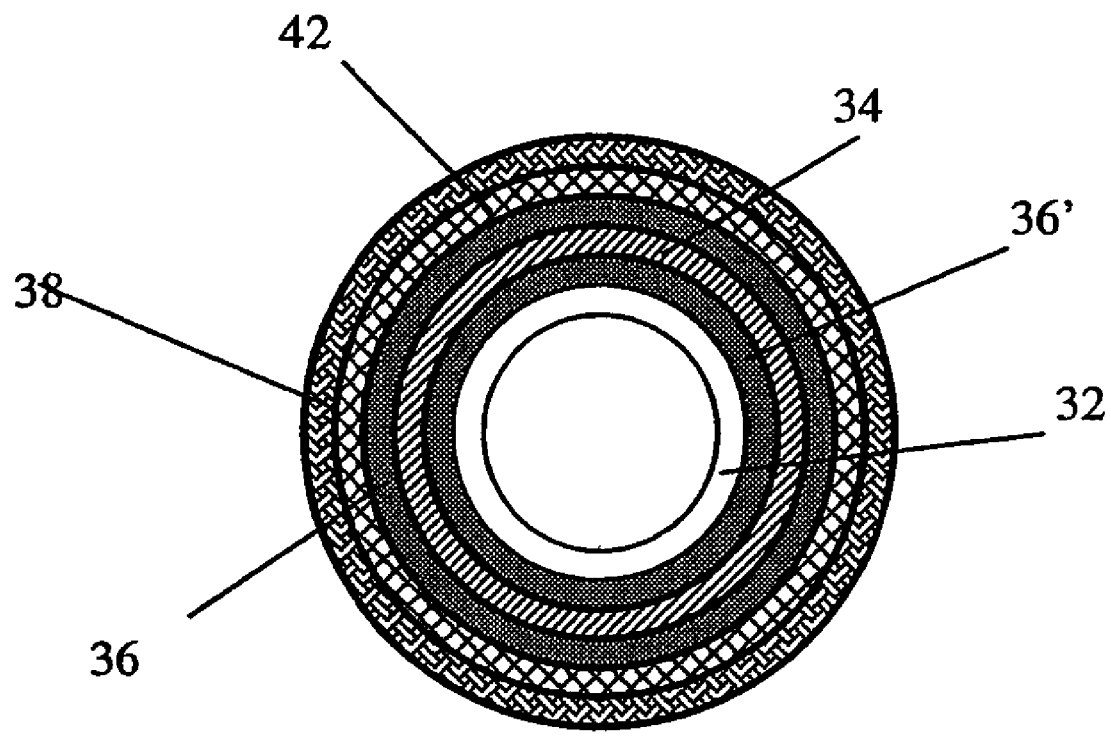

Furthermore, with reference to FIGS. 4d and 4e, there are shown a cross-section view of another embodiment of the stent/graft of the present invention with the reinforcement member 38 securely attached to the outer layer of the graft. The stent/graft 40 comprises all the layers as shown in FIG. 3b with an addition of a tubular support structure, preferably a stent 42 as shown in FIG. 4d and FIG. 4e. In FIG. 4d, the stent 42 is located on the inside surface of the graft with reinforcement member 38 attached to the outer layer of the graft. Alternatively, the stent 42 can be located on the outside surface of the graft as shown in cross-section view of the stent/graft 40 in FIG. 4e. Again, the reinforcement member 38 is securely attached to the outer layer of the graft.

As mentioned above, the stent 42 may be of any configuration known to those skilled in the art, including those used alone or in a stent/graft arrangement. Various stent types and stent constructions may be employed in the present invention including, without limitation, self-expanding stents and balloon expandable stents. The stents may be capable of radially contracting as well. Self-expanding stents include those that have a spring-like action, which cause the stent to radially expand, or stents, which expand due to the memory properties of the stent material for a particular configuration at a certain temperature. Nitinol® is an example of a material which may be used as a self-expanding stent. Other materials are of course contemplated, such as stainless steel, platinum, gold, titanium, tantalum, niobium, and other biocompatible materials, as well as polymeric stents. The configuration of the stent may also be chosen from a host of geometries. For example, wire stents can be fastened in a continuous helical pattern, with or without wave-like forms or zigzags in the wire, to form a radially deformable stent. Individual rings or circular members can be linked together such as by struts, sutures, or interlacing or locking of the rings to form a tubular stent.

Figure 4F:
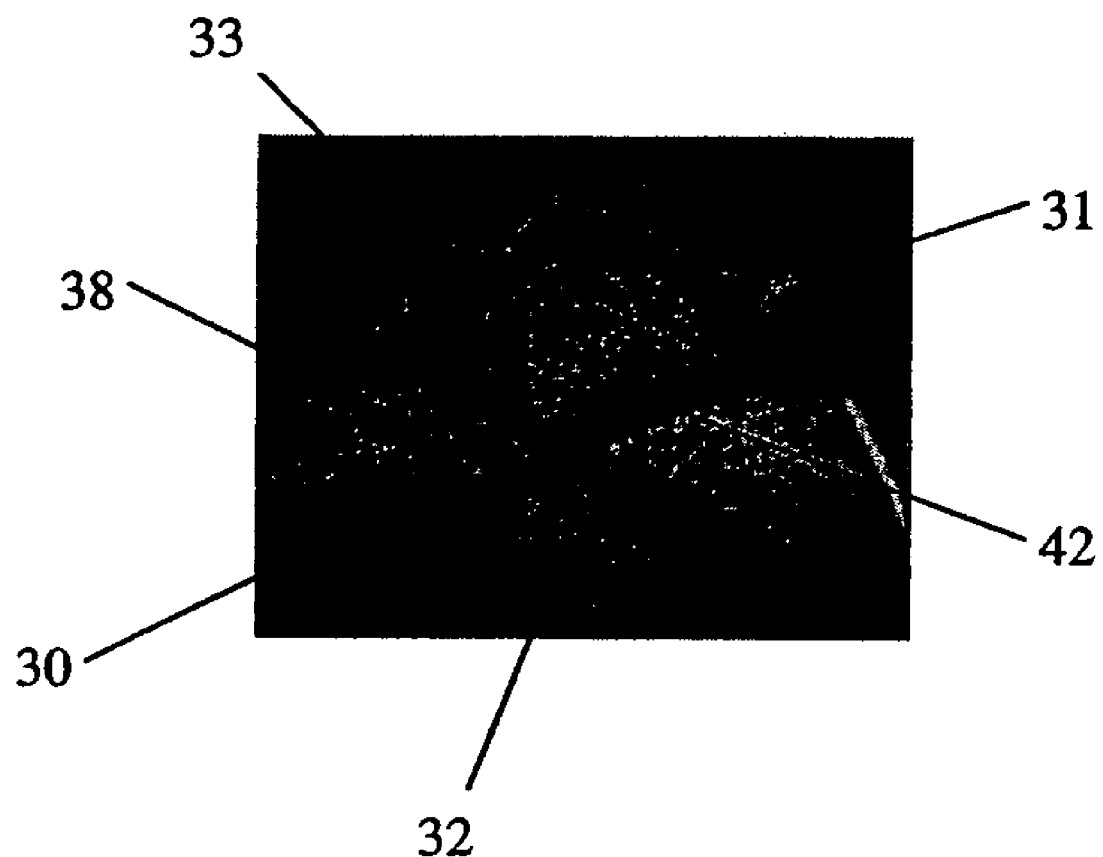
FIG. 4f is an enlarged view of one end of the stent/graft of the present invention.

FIG. 4f is an enlarged view of one end of a stent/graft 40 of the present invention after it has been inverted to more clearly show the stent and its attachment to the reinforced attachment sites at the graft end(s). This enlarged view clearly shows the device 40 having the stent 42 on the inside surface of the graft. In particular, the stent is positioned adjacent to ePTFE layer 32 and reinforcement member 38. The reinforcement member is bonded to the inside surface of layer 32 in this embodiment. The ePTFE layer 32 is preferably an inner member/layer of a hybrid covering. The hybrid covering also includes an outer knit textile layer (not shown). The graft 30 is attached to stent 42 with stitching material 31 at graft end(s) 33. The ends 33 define the attachment site for attaching the graft 30 to stent 42. The reinforcement member 38, of preferably textile material, is clearly shown as attached to the inside of the hybrid covering. The reinforcement member 38 can also include other materials, such as polymer sleeve, ePTFE or like. Also, the graft 30 can be sutured to the stent 42 at one or both of the graft ends. At the attachment site, the textile or other material is stressed, which over time, causes the suture or stitching material 31 to elongate the suture hole in the covering. As mentioned before, member 38 acts as a reinforcement to provide for reinforcing the attachment sites of graft or hybrid graft materials that are used as stent-graft coverings. The member 38 prevents the elongation of the suture hole in the covering and therefore prevents the device from losing its integrity.

As discussed above, the reinforcement members (element 18 of FIG. 1 or 38 of FIGS. 3a, 3b, 4a, 4b, 4c and 4d) establish a reinforced attachment site for said stent/graft prosthesis. These reinforcements can be placed at the inside surface of the graft (FIGS. 3a, 4a, 4b and 4c), at the outside surface of the graft (FIGS. 3b, 4d, and 4e) or at both the inside and outside surfaces of the graft (not shown). Also, the reinforcements as shown in the drawings are attached to at least one end of the graft or stent/graft, preferably at both ends of the graft. Furthermore, they can be placed throughout the stent-graft covering as required by the design. Moreover, the rein-forcement member can be positioned so that it encapsulates the stent wires, thereby eliminating the need for sutures or stitching, if desired.

Figure 5A:
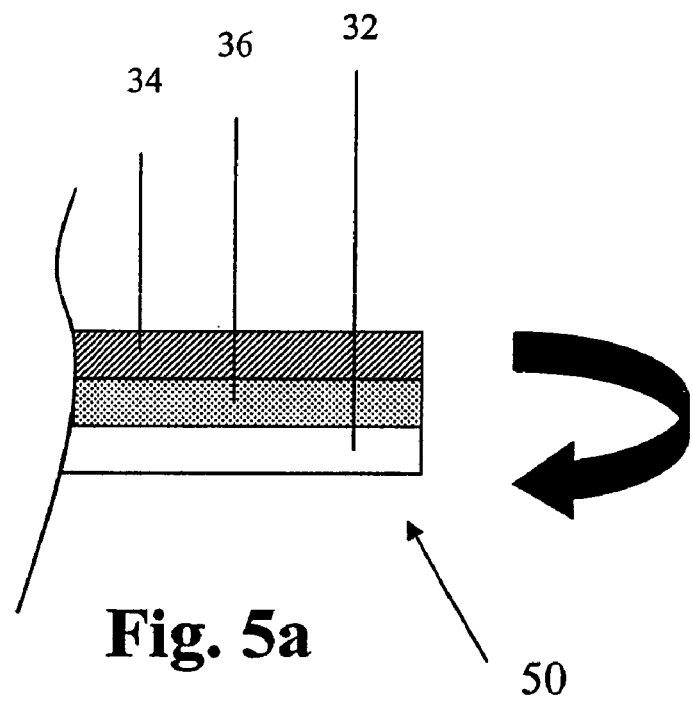
FIGS. 5a-5k show longitudinal schematic cross-section views of alternate embodiments of the graft and the stent/graft of the present invention.
Figure 5B:
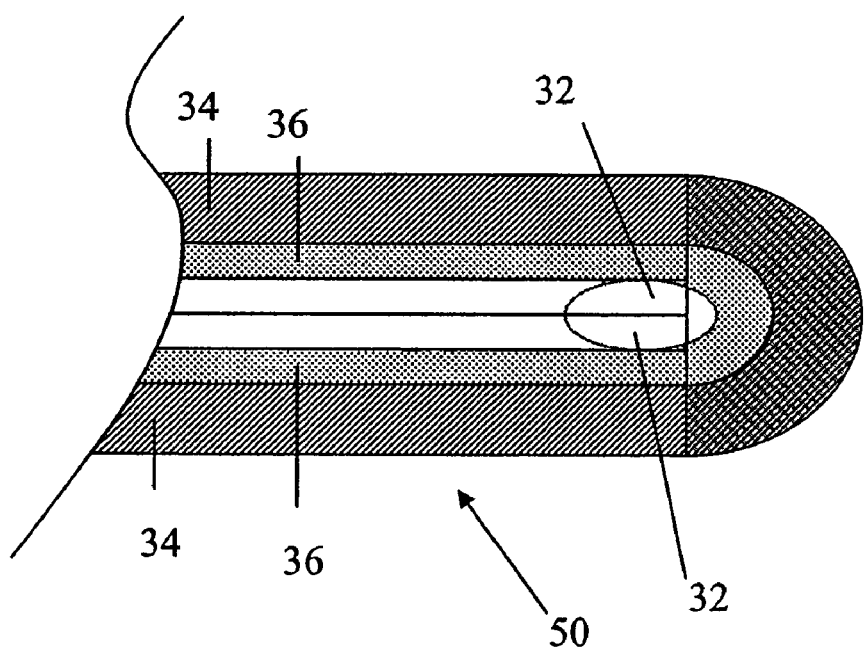
Figure 5C:
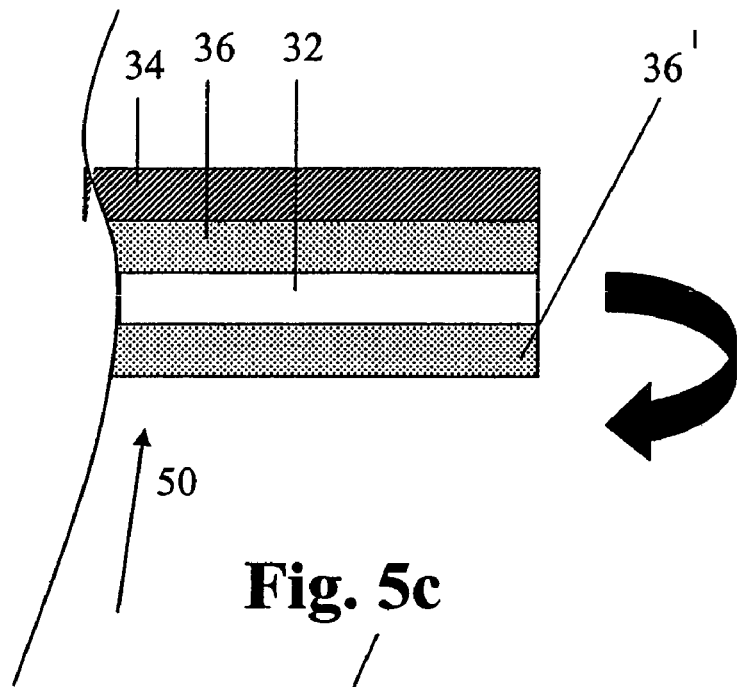
Figure 5D:
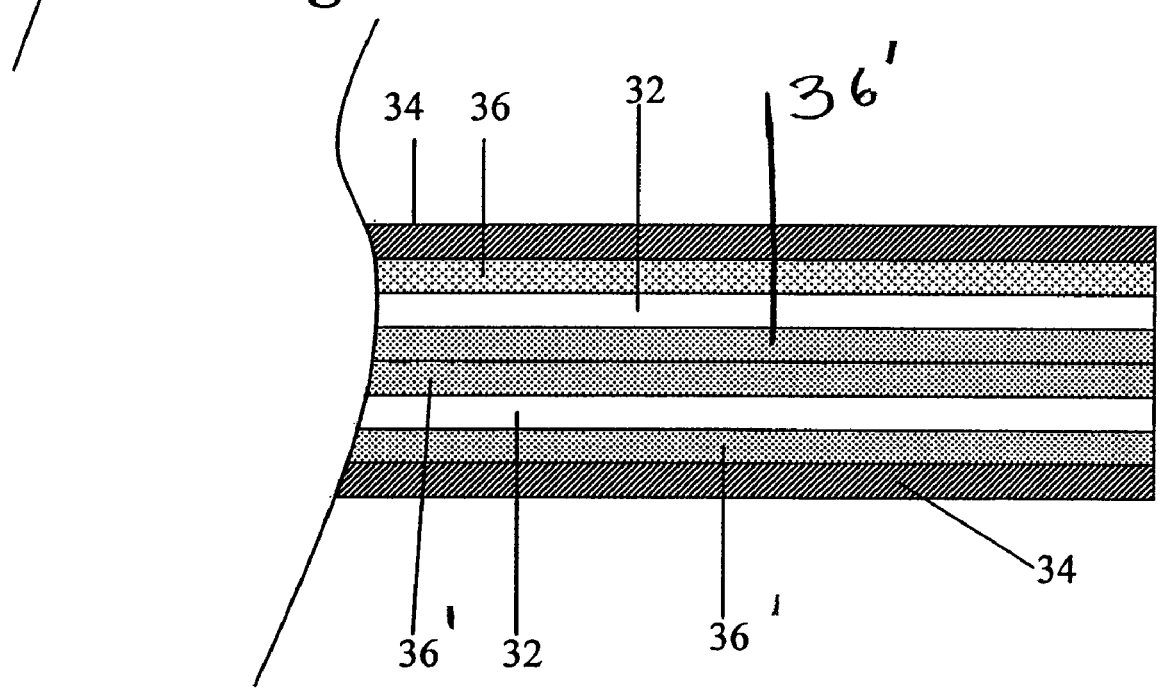

Referring to FIG. 5a of the present invention, there is shown a schematic view of graft 50 having an inner ePTFE layer 32 bonded to the outer textile layer 34 with the layer of bonding agent 36 as shown. The arrow in FIG. 5a indicates that the graft will be folded over itself as shown in FIG. 5b. After the graft is folded as shown in FIG. 5b, the end may preferably be glued or sutured to itself. The entire folded portion of the graft 50 forms a reinforcement. Alternatively, FIG. 5c shows the schematic view of the graft 50 which preferably includes an additional bonding agent 36' such as an adhesive, bonded or coated to the inside surface of the body. As indicated by the arrow, the graft 50 is now folded over itself with the bonding agent 36', as shown in FIG. 5d, thereby forming a reinforcement.

Figure 5E:
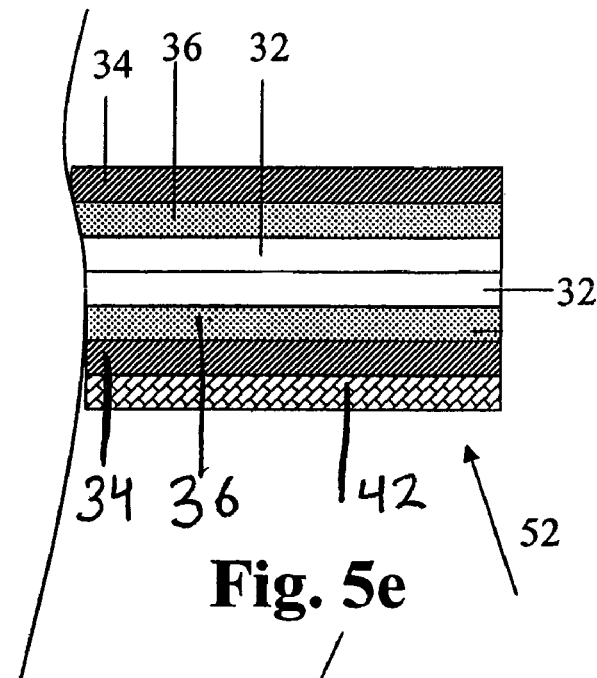
Figure 5F:
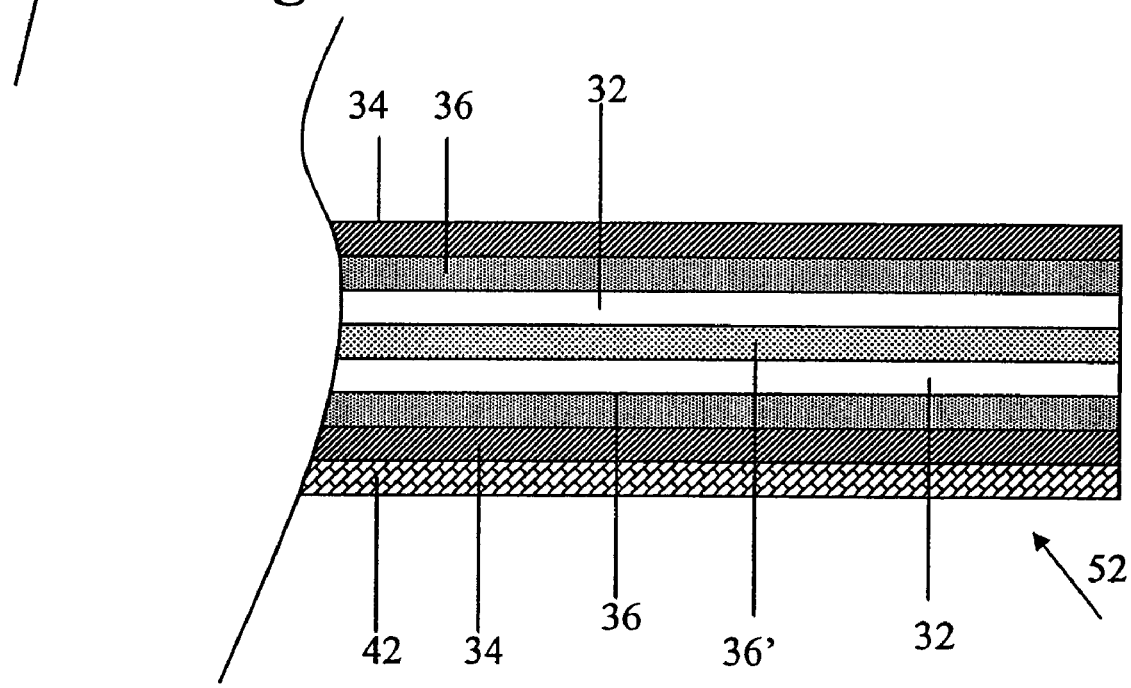

In a further embodiment of the present invention, there is shown a schematic view of the folded stent/graft 52 in FIG. 5e with a graft similar to the graft 50 with stent 42 located inside the graft 50. The graft 50 is preferably stitched to the stent 42. In this embodiment, the graft 50 is folded over itself externally and bonded, stitched or sutured to itself and the stent 42, again to form a reinforcement. Alternatively, FIG. 5f shows a schematic view of the folded stent/graft 52. The graft 50 is folded over itself externally with an additional bonding agent 36' and again, bonded, stitched or sutured to itself and the stent 42.

Figure 5G:
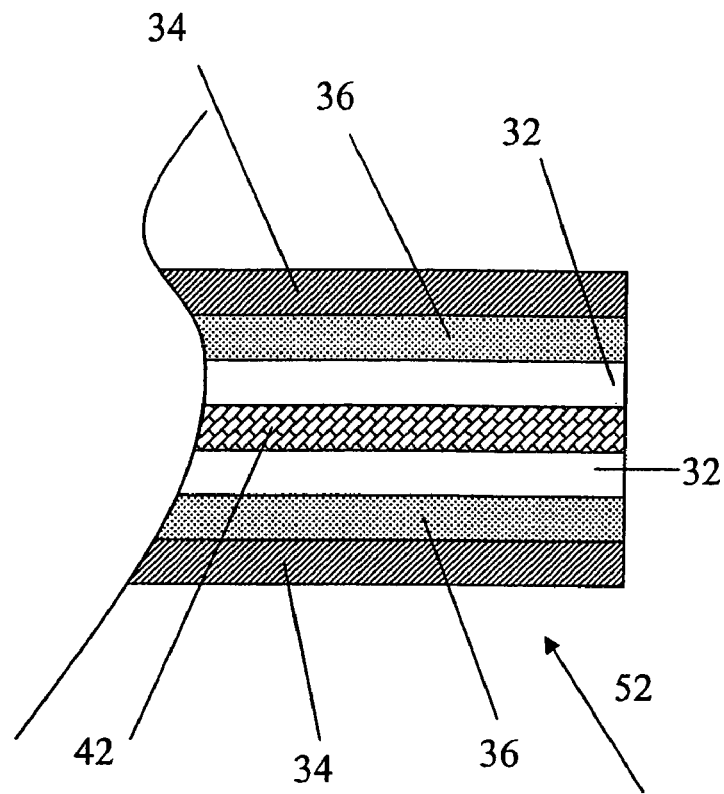
Figure 5H:
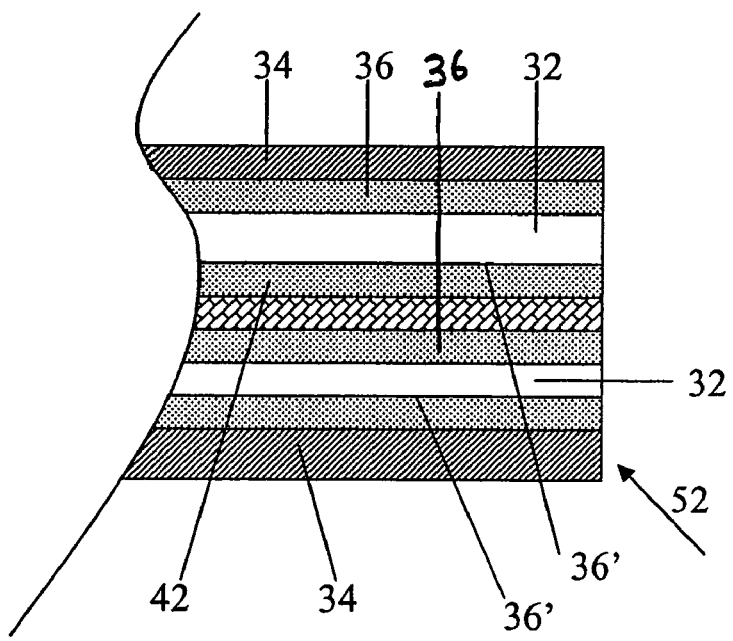

In an additional embodiment of the present invention, there is shown a schematic view of the folded stent/graft 52 in FIG. 5g with stent 42 located between the graft material. In this embodiment, the graft 50 is folded over itself internally and bonded, stitched or sutured to itself and the stent 42. Alternatively, FIG. 5h shows a schematic view of the folded stent/graft 52 similar to the one in FIG. 5g, however, the graft 50 is folded over itself internally with the additional bonding agent 36' and further bonded, stitched or sutured to itself and the stent 42.

Figure 5I:
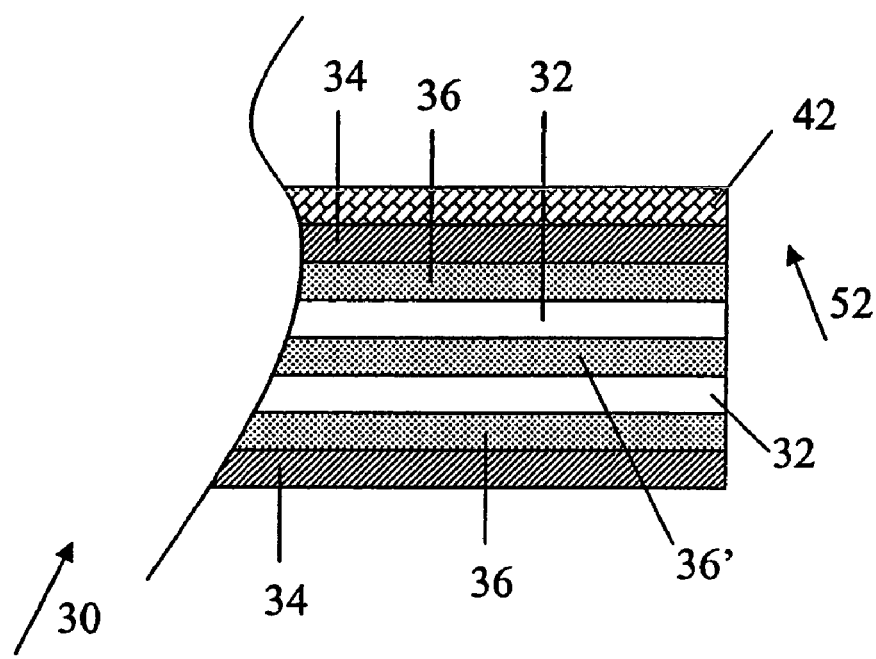

In another embodiment of the present invention, there is shown a schematic view of the folded stent/graft 52 in FIG. 5i having the additional bonding agent 36' with the stent 42 located on the outside of the graft 50. Graft 50 is folded over itself with the additional bonding agent 36' and stitched to the stent 42.

Figure 5J:
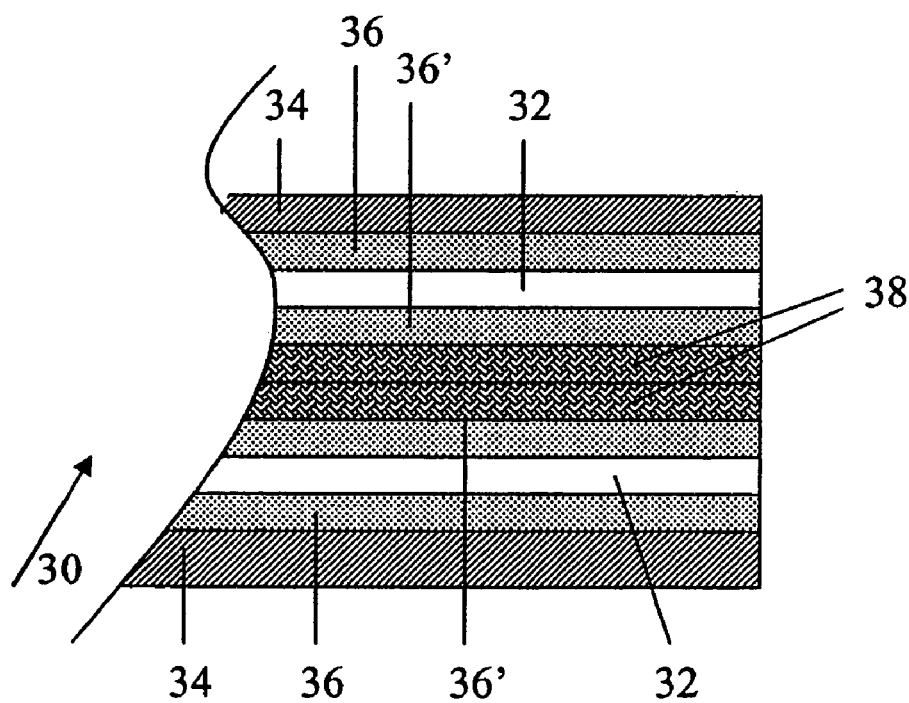
Figure 5K:
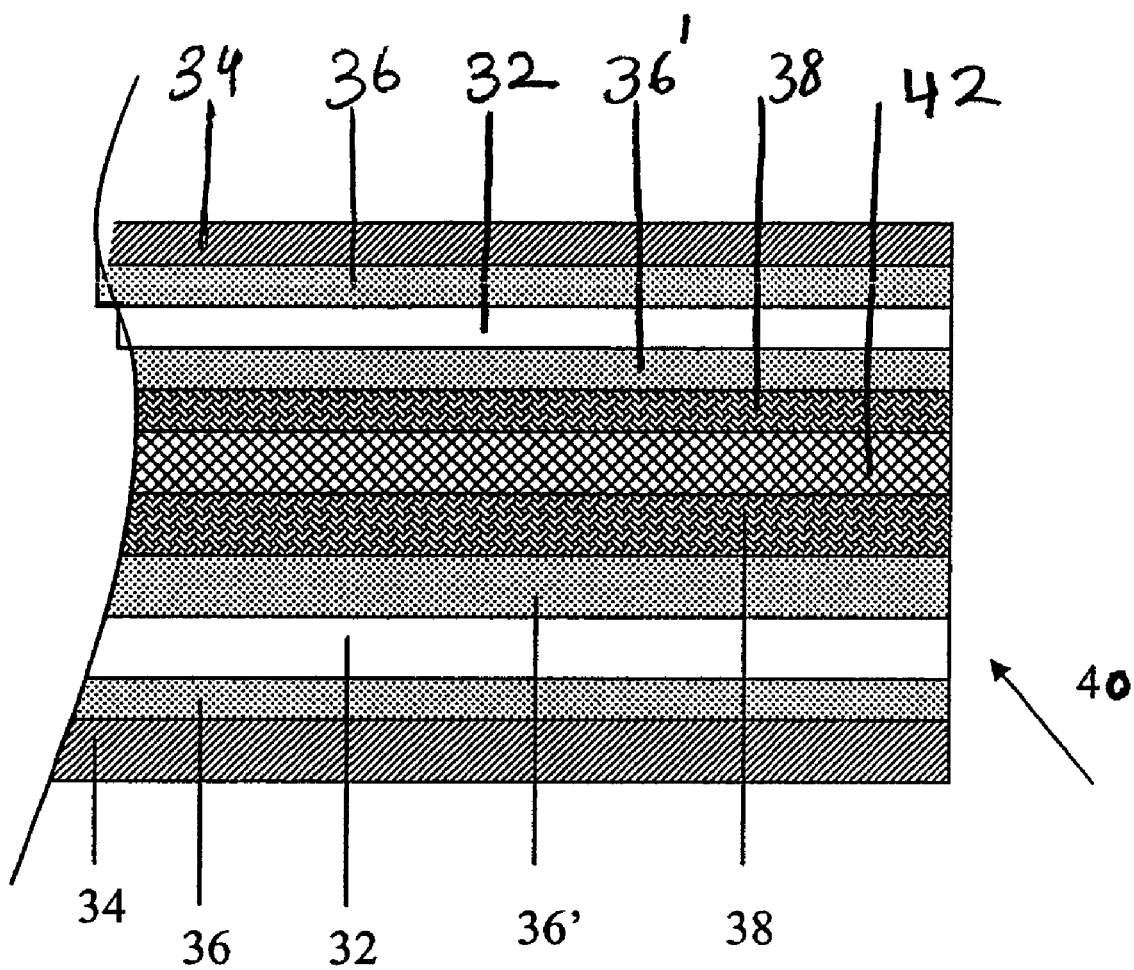

In a further embodiment of the present invention, FIG. 5j shows a schematic view of the folded graft 30. This graft 30 is similar to the one in FIG. 3a with the reinforcement member 38, located inside the graft however the graft 30 is folded over onto itself and again glued or sutured to itself. In an even further embodiment, there is shown a schematic view of the folded stent/graft 40 in FIG. 5k with the stent 42 disposed in the graft 30 and bonded between the reinforcement member 38, where the graft 30 is folded over onto itself and bonded, stitched or sutured to itself and the stent.

The textile portions of the present invention can have virtually any textile construction, including non-woven, weaves, knits, braids, filament windings and the like. Desirably, textile portions 34 and 38 are woven textile portions. Any known weave pattern in the art, including, simple weaves, basket weaves, twill weaves, satin weaves, velour weaves and the like may be used.

Desirably, textile portions 34 and 38 are knitted textile portions. Knitting involves the interlooping or stitching of yarn into vertical columns (wales) and horizontal rows (courses) of loops to form the knitted fabric structure. Warp knitting is particularly useful with the knitted textile portions of the present invention. In warp knitting, the loops are formed along the textile length, i.e., in the wale or warp direction of the textile.

Knitting patterns useful with the present invention include conventional warp-knitted patterns and high-stretch, warp-knitted patterns. Commonly used warp-knitted patterns include locknit (also referred to as tricot or jersey knits), reverse locknit, sharkskin, queenscord and velour knits. Useful high stretch, warp-knitted patters include those with multiple patterns of diagonally shifting yarns, such as certain modified atlas knits which are described in U.S. Pat. No. 6,540,773, the contents of which are in incorporated herein by reference. Other useful high-stretch, warp knitted patterns include certain patterns with multiple needle underlap and one needle overlap, such as those patterns described in U.S. Pat. No. 6,554,855 and U.S. patent application Ser. No. 10/410,482, entitled "Low Profile, High Stretch, Low Dilation Knit Prosthetic Device", filed on Apr. 9, 2003, the contents of which are incorporated herein by reference.

The prostheses of the present invention may be coated with a bio-absorbable coating, such as collagen, albumin, elastin and the like. Such coatings are known in the art and are desirable in vascular and endovascular graft applications to seal the graft and thereby prevent blood loss in the early stages of implantation. Other coatings which may be used include those disclosed in U.S. Pat. No. 5,851,229, which is incorporated herein. The '229 patent discloses a sealant composition that includes at least two polysaccharides in combination to form a hydrogel or solgel. Sealant compositions may include a bioactive agent and or be cross-linked subsequent to the application of these compositions to the substrate surface. Additionally, U.S. Pat. No. 5,209,776, incorporated herein, discloses a composition that includes a first protein component that is preferably collagen and a second protein-supporting component that can be a proteoglycan, a saccharide or a polyalcohol.

Axial yarns are added in some cases to limit a textile structure from stretching beyond a desired amount, and thereby significantly reducing the potential for scissoring action of the yarns. This scissoring or shearing action is detrimental to the body's healing process. The scissoring action of the strands tends to prevent the tissue and blood vessels from infiltrating the pores of the structure. Additionally, an axial yarn may be dyed and inserted into the textile structure subsequent to or during the braiding process. A dyed axial yarn positioned in the outer surface of the prosthesis aids the surgeon during implantation to indicate whether the prosthesis is straight and not twisted during the procedure.

A knitted textile graft of the present invention is desirably made on a warp-knitting machine (not shown) using a double needle bar. A useful number of needles per inch for warp knitting is from about 18 to about 36. About 28 to 30 needles per inch are particularly suitable. The trellis of the graft is usually made from a yarn having count from 30 to 300 denier. Desirably, the range of yarn counts for the trellis is from about 30 to about 80. A particularly suitable yarn count is about 40 denier. Moreover, the trellis yarn may be a single ply, a double ply or a multi-ply. The term "multi-ply" is used herein to indicate more than two-ply.

In one aspect of the present invention, a knitted textile graft is a knit structure of a single layer with at least a two-needle underlap. Because of the single layer construction, the textile wall thickness is minimized to yield a low profile knitted textile graft. The textile wall thickness is from about 0.2 to about 0.4 millimeters. Desirably, the textile wall thickness is from about 0.27 to about 0.31 millimeters. Furthermore, the knitted textile graft of the present invention has a burst strength from about 11 kg/cm$^2$ to about 16 kg/cm$^2$ (about 150 psi to about 220 psi). Desirably, the knitted textile graft of the present invention has a burst strength from about 13 kg/cm$^2$ to about 14 kg/cm$^2$ (about 170 psi to about 190 psi). The stretchability of the knitted textile graft is desirably from about 5 to about 150 percent at a one-kilogram of load, more desirably about 50 to about 100 percent at one-kilogram load.

Any type of textile product can be used as yarns for the knitted or woven portions of the present invention. Of particular usefulness in forming the fabric portions of the present invention are synthetic materials such as synthetic polymers. Synthetic yarns suitable for use in the present invention include, but are not limited to, polyesters, including PET polyesters, polypropylenes, polyethylenes, polyurethanes and polytetrafluoroethylenes. The yarns may be of the monofilament, multifilament, spun type or combinations thereof. The yarns may also be flat, twisted or textured, and may have high, low or moderate shrinkage properties or combinations thereof.

The yarns used in forming the textile grafts of the present invention may be flat, twisted, textured or combinations thereof. Furthermore, the yarns may have high, low or moderate shrinkage properties or combination of different shrinkage properties. Additionally, the yarn type and yarn denier can be selected to meet specific properties desired for the prosthesis, such as porosity and flexibility. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 200, preferably from about 30 to about 100. Preferably, the yarns are polyester, such as polyethylene terephthalate (PET).

Moreover, stent-graft 40 of FIG. 4 may be formed as an implantable prosthesis which is self-supporting and usable to maintain patency of a bodily vessel, such as in the coronary vasculature, esophagus, trachea, colon, biliary tract, urinary tract, prostate, and brain. Also, the textile portion 34 and 38 or the yarns forming textile portion may be treated with any of the following therapeutic agents: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promoters (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin);

cholesterol-lowering agents; vasodilating agents; and agents which interfere with endogenous or vasoactive mechanisms.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An implantable graft comprising:
an elongate graft tube having opposed ends and a tubular wall therebetween having an inner wall layer comprising a first material and an outer wall layer comprising a second material different than the first material, the first material being expanded polytetrafluoroethylene (ePTFE) and the second material being a textile material, said outer wall layer being attached to said inner wall layer such that said outer wall layer directly contacts said inner wall layer, a portion of said outer wall layer defining an attachment site for attaching said graft tube to a stent; and
a reinforcement member attached to said outer wall layer such that said reinforcement member directly contacts said attachment site, said reinforcement member reinforcing said attachment site wherein said reinforcement member comprises a separate ring of material for strengthening the attachment site, said reinforcement member having a longitudinal dimension defined by opposed end edges which is less than a longitudinal dimension defined by the opposed ends of said graft tube.

2. The graft of claim 1, wherein said stent is stitched to the graft.

3. The graft of claim 1, wherein said stent is sutured to the graft.

4. The graft of claim 1, wherein the textile material of the outer wall layer being a knitted material.

5. The graft of claim 1, wherein said reinforcement member is a knitted textile material.

6. The graft of claim 1, wherein said reinforcement member is a woven textile material.

7. The graft of claim 1, wherein said reinforcement member is a braided textile material.

8. The graft of claim 1, wherein said reinforcement member is an expanded polytetrafluoroethylene (ePIFE).

9. The graft of claim 1, wherein said reinforcement member is bonded to said graft with adhesive bonding.

10. The graft of claim 1, wherein said reinforcement member is bonded to said graft with ultrasonic bonding.

11. The graft of claim 1, and further comprising an elastomeric coating applied to said attachment site.

12. The graft of claim 1, wherein the stent has an elongate structural member, said reinforcement member being shaped to define an enclosure for encapsulating the structural member.

13. The graft of claim 1, wherein said end of said outer wall layer which defines said attachment site is folded.

14. The graft of claim 13, wherein said reinforcement member is located within said folded end of said outer wall layer.

15. A graft, the graft comprising a tubular portion and at least one reinforcement member;
the tubular portion having a first end, a second end, an inner surface, an outer surface, a longitudinal length, the tubular portion comprising:
a first tube made of ePTFE; and
a second tube made of a textile material;
the first tube being bonded to the second tube by a layer of bonding agent;
each reinforcement member having a first surface, the entire first surface being bonded to a portion of one of the surfaces of the tubular portion, each reinforcement member being a ring made of a textile material, each reinforcement member having a longitudinal length less than the longitudinal length of the tubular portion.

16. The graft of claim 15, a first surface of the first tube forming the inner surface of the tubular portion and a first surface of the second tube forming the outer surface of the tubular portion.

17. The graft of claim 15, further comprising a stent, the stent being engaged to the graft at least one attachment site.

18. The graft of claim 17, the stent being engaged to the inner surface of the tubular portion.

19. The graft of claim 17, the stent being engaged to the at least one attachment site by stitching or suturing.

20. The graft of claim 17, the at least one reinforcement member being engaged to or adjacent to the at least one attachment site.

21. The graft of claim 17, the at least one attachment site comprising a first attachment site and a second attachment site, the first attachment site being positioned at the first end of the tubular portion and the second attachment site being positioned at the second end of the tubular portion.

22. The graft of claim 15, the textile material being made of a synthetic yarn.

23. The graft of claim 22, the synthetic yarn being selected from at least one member of the group consisting of polyesters, polypropylenes, polyethylenes, polyurethanes, polynaphthalenes, and polytetrafluoroethylenes.

24. The graft of claim 22, the synthetic yarn of the second layer being a thermoplastic material.

25. The graft of claim 15, the textile material of the second layer either being woven, knitted, or braided.

26. The graft of claim 15, the textile material having a thickness of about 0.2 mm to about 0.4 mm.

27. The graft of claim 15, the textile material having a burst strength from about 11 kg/cm$^2$ to about 16 kg/cm$^2$.

28. The graft of claim 15, the bonding agent being a biocompatible elastomeric bonding agent.

29. The graft of claim 15, the at least one reinforcement member being engaged to the inner surface of the graft.

30. The graft of claim 15, the at least one reinforcement member comprising a plurality of reinforcement members, at least one of the plurality of reinforcement members being engaged to the inner surface of the graft and at least one of the plurality of reinforcement members being engaged to the outer surface of the graft.

31. The graft of claim 15, the at least one reinforcement member being engaged to the tubular portion adjacent to at least one of the ends of the tubular portion.

* * * * *